US00PP31941P3

(12) United States Plant Patent
Flagg-Miller

(10) Patent No.: US PP31,941 P3
(45) Date of Patent: Jul. 7, 2020

(54) GARLIC PLANT DENOMINATED 'MMG1'

(50) Latin Name: ***Allium sativum* L**
Varietal Denomination: MMG1

(71) Applicant: Allyson Jayne Flagg-Miller, Corvallis, OR (US)

(72) Inventor: Allyson Jayne Flagg-Miller, Corvallis, OR (US)

( * ) Notice: Subject to any disclaimer, the term of this patent is extended or adjusted under 35 U.S.C. 154(b) by 0 days.

(21) Appl. No.: 15/932,116

(22) Filed: Feb. 6, 2018

(65) Prior Publication Data

US 2019/0246544 P1 Aug. 8, 2019

(51) Int. Cl.
*A01H 5/00* (2018.01)
*A01H 6/04* (2018.01)

(52) U.S. Cl.
USPC ..... Plt./258
CPC ..... *A01H 6/04* (2018.05)

(58) Field of Classification Search
USPC ..... Plt./258, 263.1
CPC ... A01H 5/06; A01H 5/12; A01H 5/02; A01H 5/08; A01H 5/00; A01H 5/04; A01H 6/04; A01H 6/045
See application file for complete search history.

(56) References Cited

PUBLICATIONS

Schmitz. Farmer unearths rare garlic, Capital Press 2011, retrieved on Jan. 23, 2019, retrieved from the Internet at www.capitalpress.com/state/oregon/farmer-unearths-rare-garlic/article_c49c8df0-5769-5da1-a845-5b7ee4602fa7.html, 4 pp. (Year: 2011).*

* cited by examiner

*Primary Examiner* — June Hwu

(57) ABSTRACT

The unique garlic plant variety denominated 'MMG1' is provided. The variety is characterized by larger bulbs, yields 5 large spicy hot bulbs per plant, 7.5 to 8 foot in overall plant height, 12 to 18-month shelf life, 9 months from planting to harvest of the plant, high yield of bulbs, disease-free vegetation, presence very large spicy hot edible flower scape, and vigorous foliage that develops unusually larger bulbs and scapes.

6 Drawing Sheets

Latin name and variety denomination: The present disclosure elates to a new and distinct variety of *Allium sativum* L, which is hereby denominated 'MMG1'.

BACKGROUND

The present invention relates to a new and distinct cultivar of garlic plant, botanically known as. and hereinafter referred to by the cultivar name 'MMG1'.

'MMG1' was originally found in a cultivated state and was asexually propagated and selected with the objective of identifying individuals having early harvesting capabilities, large clove arrangements, and healthy plant material. 'MMG1' has been asexually reproduced in Turner, Oreg., via clove-propagated asexual reproduction and cultivation. The clones so produced have been observed through several growing seasons and the clones are identical to the parent plant in all characteristics.

Characterized by larger bulbs, yields 5 large spicy hot bulbs per plant, 7.5 to 8 foot in overall plant height, 12 to 18 month shelf life, 9 month from planting to harvest of the plant, disease-free vegetation, presence very large spicy hot edible flower scape, and vigorous foliage that develops unusually larger bulbs and scapes.

The following traits have been repeatedly observed and are determined to be basic characteristics of 'MMG1' which in combination distinguish this garlic as a new and distinct cultivar:

9 month harvesting of the plant;

Disease-free vegetation;

Presence of large, hot, edible or ornamental flower scape; and

Vigorous foliage that develops quicker and has more volume than comparative cultivars.

Cloves are hot and spicy to the taste and are medicinal.

'MMG1' has not been observed under all possible environmental conditions. The phenotype of the new cultivar may vary significantly with variations in environment such as day length, temperature, soil condition, humidity, fertilization and date of planting without any change in genotype of the cultivar. The following observations, measurements, and comparisons describe plants grown in the Willamette Valley, Oreg. under conditions that approximate those generally used in commercial practice. The age of the plants described is 9 months after planting.

Of the many commercial cultivars known to the present inventor, the most similar in comparison to 'MMG1' is 'Elephant Garlic' (never patented). In comparison to 'Elephant Garlic', 'MMG1' has similar bulb and clove colors but demonstrates significant differences in the earliness of harvesting, larger bulbs, larger scape, both scape and bulbs are very hot to the taste, longer shelf life, higher yield and healthier cultivation and culinary values.

BRIEF DESCRIPTION OF THE DRAWINGS

The present variety will become more fully understood from the detailed description and the accompanying drawings, wherein.

DETAILED BOTANICAL DESCRIPTION

Figure 1:
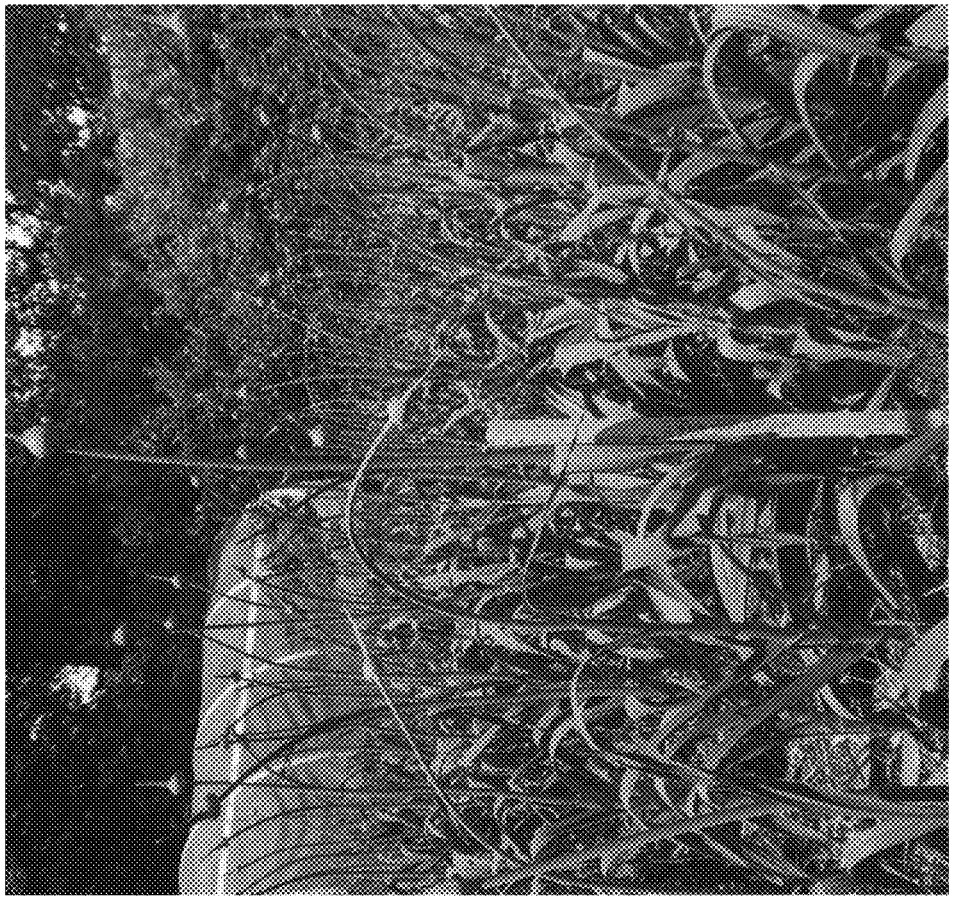
FIG. 1 is a photographic print in full color of a first perspective of 'MMG1', wherein the plant is in the foreground and the additional plants or portions thereof in the background and the grass on the ground are not part of 'MMG1'.
Figure 2:
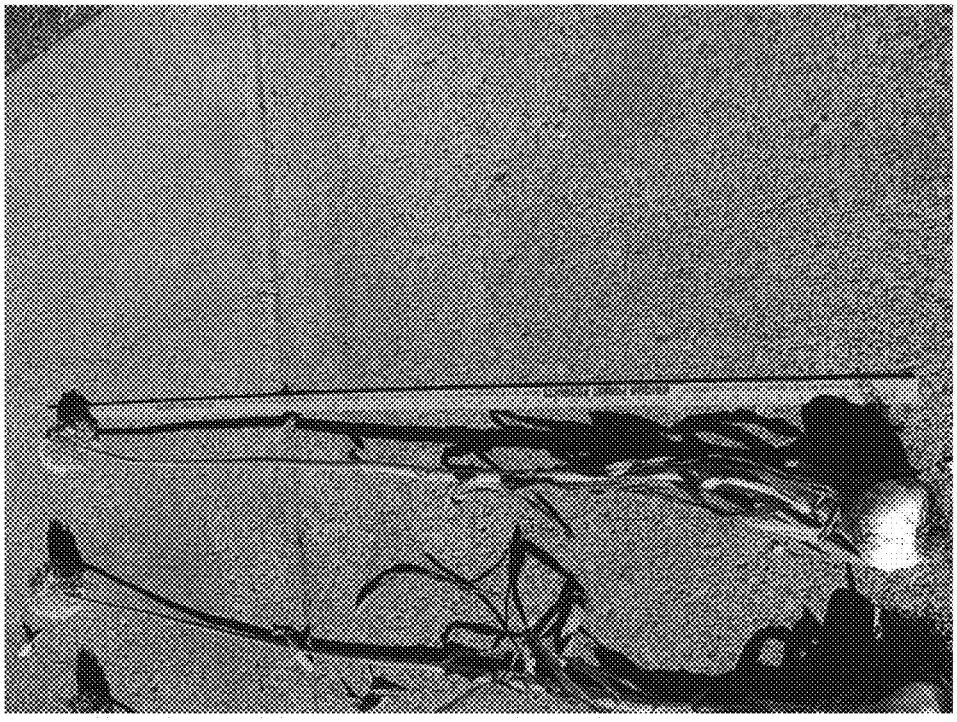
FIG. 2 is a photographic print in full color of a second perspective of a 'MMG1' plant, wherein the plant has been harvested.
Figure 3:
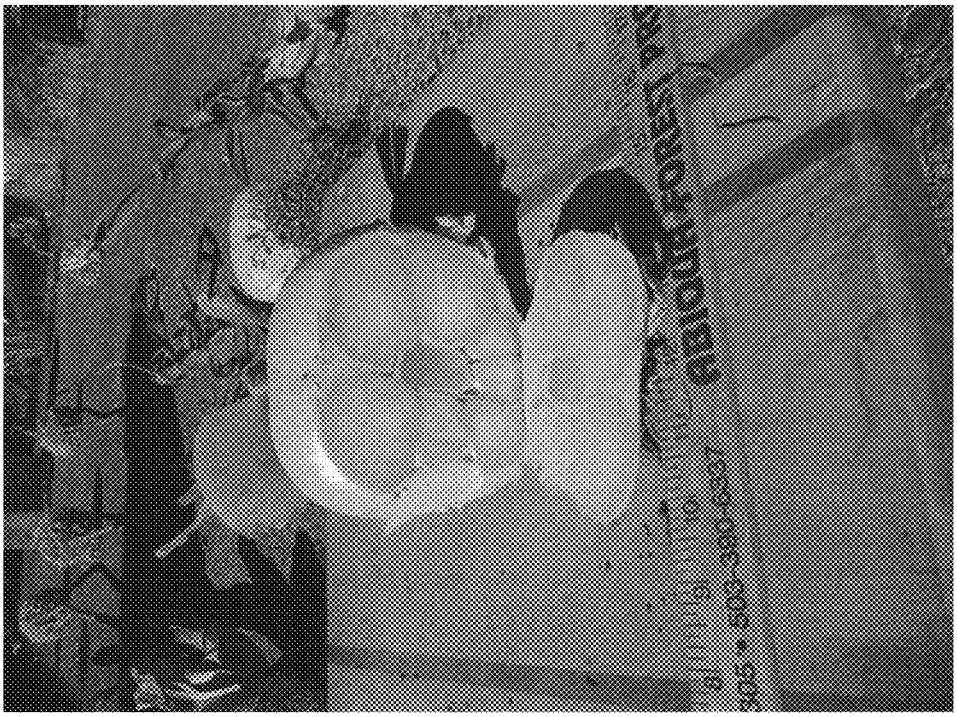
FIG. 3 is a photographic print in full color illustrating a first 'MMG1' sectional view of bulb clusters, wherein the bulbs shown are mature.
Figure 4:
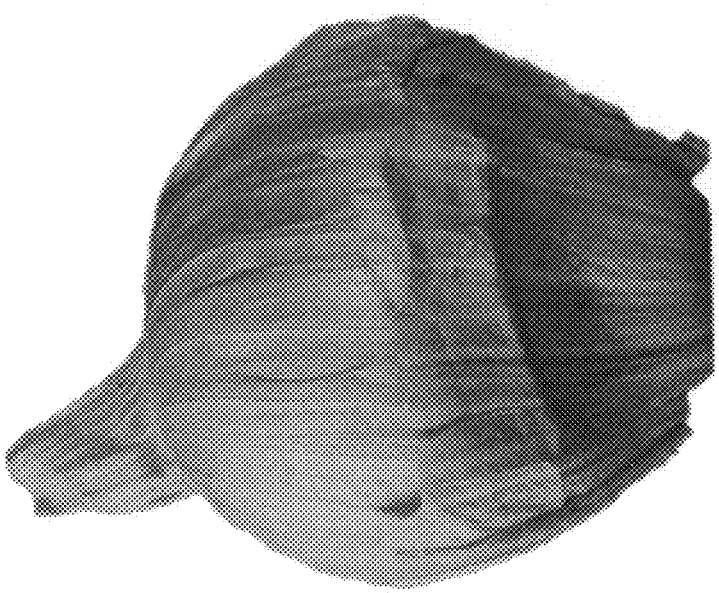
FIG. 4 is a photographic print in full color illustrating a second 'MMG1' bulb with exemplary bulb clusters; wherein most, but not all, of the bulb shown are mature.
Figure 5:
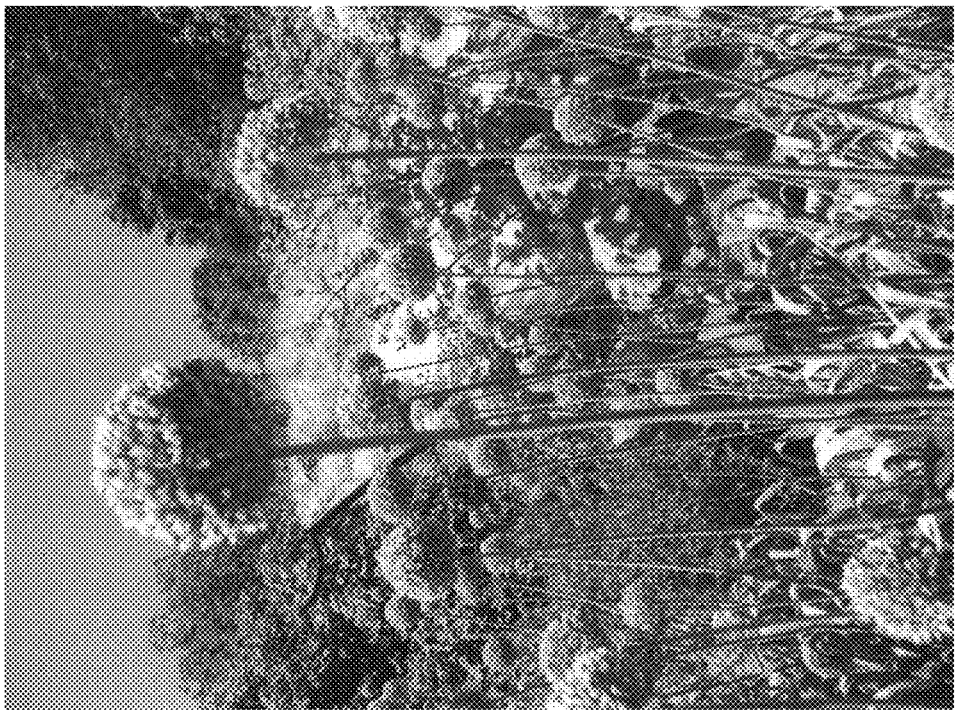
FIG. 5 is a photographic print in full color illustrating a second 'MMG1' umbel.
Figure 6:
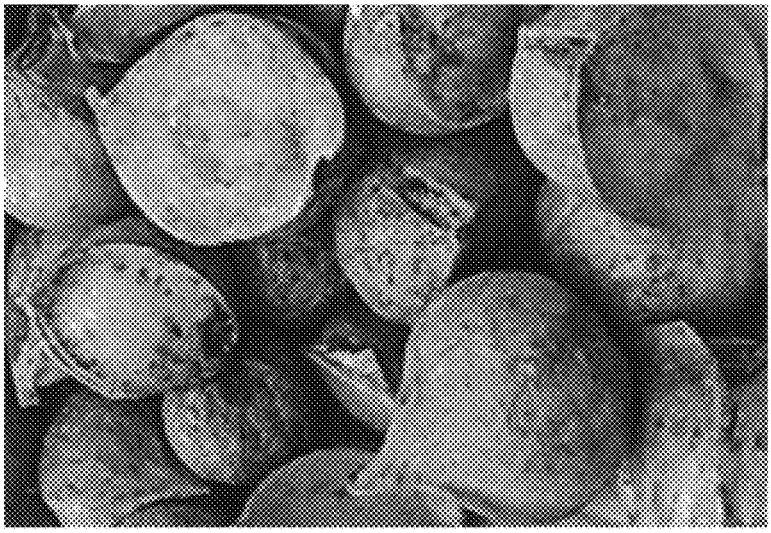
FIG. 6 is a photographic print in full color illustrating cloves (divided segments of bulbs) of 'MMG1' as used for asexual propagation.

The following observations, measurements and values describe the cultivar as grown in the Willamette Valley, Oreg., under conditions which closely approximate those generally used in commercial practice. Color designations are based on The R.H.S. Colour Chart.

Origin: Grape Lane Poultry Farm, Willamette Valley, Oreg.

Parentage: Unknown.

Classification:

*Botanical.*—*Allium sativum* L.

Plant: Garlic.

*Form.*—Bulbous herb.

*Height including umbel.*—6.5 to 7 feet, depending on cultivation conditions. when grown in Willamette Valley, Oreg.

*Growth habit.*—Fast response, very vigorous growth and volume (in comparison to standard variety 'Elephant Garlic'.

*Harvest/typical growing season.*—In one growing season only one harvest takes place. The typical growing season is from October to July in Western United States climate conditions and from October to June in sub-Mediterrane.an conditions.

*Blooming season.*—Late May-mid June.

*Average time of harvest.*—August.

*Plant hardiness zone.*—Zone 7a.

Foliage:

*Quantity.*—Up to 11 leaves depending on cultivation conditions.

*Size.*—Minimum leaf length is 3 feet, maximum leaf length is 5 feet, depending on cultivation conditions.

*Shape of leaf.*—Elongated.

*Aspect.*—Arched to hanging.

*Color.*—Light emerald green for both upper and lower leaf surfaces. 142A.

*Leaf width.*—Small taper from plant stem broadening to a wider center of 4 to 6 inches before tapering to a pointed tip.

*Apex.*—Acute.

*Base.*—Sessile.

*Texture.*—Satin.

*Stem coloration.*—Converts from emerald green to light green. 142A.

Scape:

*Length.*—9" to 12" depending on cultivation conditions.

*Diameter.*—⅜-½".

*Color.*—RHS 160A.

*Color.*—Purple flower 72A.

Umbels: Large umbels that shed their spathes at maturity; 4" average size, 200 average number of flowers.

*Bulbils.*—Rare. When present are ⅝" average size, globe shape, RHS 73A color.

*Spathe.*—Sheds at maturity of plant.

*Bulb shape.*—Spherical; rounded at base.

*Size.*—Average of 3-4" diameter, depending on cultivation conditions; average height 2-3".

Bulb position: Slightly depressed.

*Average bulb yield per plant.*—6.

*Color.*—Cream color to light golden. 8D.

*Number of cloves.*—5 to 6.

*Clove color.*—White. 8D.

*Clove skin color.*—Golden yellow. 162A.

*Clove shape.*—Transversely in triangular shape with round edges.

*Clove length.*—4 to 6 inches longitudinal section running to a point.

*Clove diameter.*—1-1.5 inches at the widest part.

*Clove texture.*—Glossy with and without the skin.

*Clove distribution.*—Radial.

Disease resistance: Very high for mildew, rust and botrytis. Showed stable growth and health through climate changes in weather on the Willamette Valley floor. Wetter conditions than normal.

Other characteristics: Storability over a year. Pollen. is produced.

Pseudostem: ½" average diameter, RHS 160A coloration at base.

Anthocyanin: Absent.

Flowering stem curvature: Straight.

Dry external scales ground color (white, yellowish white or reddish white): White. 15B, 42B.

Market use: Fresh.

What is claimed is:

1. A new and distinct cultivar of garlic plant named 'MMG-1', as illustrated and described.

* * * * *